United States Patent [19]

Scholl

[11] Patent Number: 4,595,534

[45] Date of Patent: Jun. 17, 1986

[54] PROCESS FOR THE PRODUCTION OF URETDIONE GROUP-CONTAINING POLYISOCYANATES

[75] Inventor: Hans-Joachim Scholl, Cologne, Fed. Rep. of Germany

[73] Assignee: Bayer Aktiengesellschaft, Leverkusen, Fed. Rep. of Germany

[21] Appl. No.: 736,572

[22] Filed: May 21, 1985

[30] Foreign Application Priority Data

May 30, 1984 [DE] Fed. Rep. of Germany ....... 3420114

[51] Int. Cl.$^4$ ........................................... C07D 499/00
[52] U.S. Cl. ................................................. 260/239 A
[58] Field of Search ..................... 260/453 P, 239 A

[56] References Cited

U.S. PATENT DOCUMENTS 3,108,100 10/1953 Tate et al. ........................... 260/248

FOREIGN PATENT DOCUMENTS

| 837636 | 3/1970 | Canada . |
| 894292 | 2/1972 | Canada . |
| 1670720 | 1/1971 | Fed. Rep. of Germany . |
| 3227779 | 1/1984 | Fed. Rep. of Germany . |
| 1200432 | 7/1970 | United Kingdom . |
| 2113673 | 8/1983 | United Kingdom . |

OTHER PUBLICATIONS

Olah, Friedel–Crafts and Related Reactions, vol. 1 (1963) pp. 228, 270.

*Primary Examiner*—Alan Siegel
*Attorney, Agent, or Firm*—Gene Harsh; Joseph C. Gil; Thomas W. Roy

[57] ABSTRACT

The present invention relates to a process for the production of uretdione group-containing polyisocyanates having aliphatically- and/or cycloaliphatically-bound isocyanate groups by dimerizing a portion of the isocyanate groups of organic diisocyanates having aliphatically- and/or cycloaliphatically-bound isocyanate groups in the presence of a dimerization-accelerating catalyst and terminating the dimerization reaction when the desired degree of dimerization in each case has been reached by addition of a catalyst poison or by the removal of the catalyst by distillation, characterized in that antimony(V)fluoride is used as the catalyst.

8 Claims, No Drawings

PROCESS FOR THE PRODUCTION OF URETDIONE GROUP-CONTAINING POLYISOCYANATES

BACKGROUND OF THE INVENTION

1. Field of the Invention

This invention relates to a new process for the production of uretdione group-containing polyisocyanates by the partial dimerization of the isocyanate groups of organic diisocyanates with aliphatically- and/or cycloaliphatically-bound isocyanate groups using antimony(V)fluoride as the dimerization catalyst.

2. Description of the Prior Art

Processes for the production of uretdiones by the dimerization of aliphatic isocyanates are known. According to DE-OS No. 1,670,720, phosphines or boron trifluoride are used as dimerization catalysts. These catalysts suffer from the disadvantage that substantial quantities of isocyanurates are formed as by-products during the dimerization reaction. According to DE-OS No. 3,227,779, certain amino-phosphines, for example tri-(dimethylamino)-phosphine, are used as dimerization catalysts for the dimerization of certain starting diisocyanates such as diisocyanatohexanes having a branched carbon chain. These aminophosphines, according to this prior publication, permit the dimerization of the particular starting diisocyanates with a substantially improved yield of uretdione groups. The production of uretdione group-containing polyisocyanates, based on other aliphatic or cycloaliphatic diisocyanates than the particular compounds mentioned above, is not disclosed in this prior publication.

Thus, an object of the present invention is to provide a new process permitting the dimerization of any organic diisocyanates having aliphatically- and/or cycloaliphatically-bound isocyanate groups in high yields without the formation of undesirable by-products.

This object may be achieved by the present process which will be described in more detail in the following.

SUMMARY OF THE INVENTION

The present invention relates to a process for the production of uretdione group-containing polyisocyanates having aliphatically- and/or cycloaliphatically-bound isocyanate groups by dimerizing a portion of the isocyanate groups of organic diisocyanates having aliphatically- and/or cycloaliphatically-bound isocyanate groups in the presence of a dimerization-accelerating catalyst and terminating the dimerization reaction when the desired degree of dimerization in each case has been reached by addition of a catalyst poison or by the removal of the catalyst by distillation, characterized in that antimony(V)fluoride is used as the catalyst.

DETAILED DESCRIPTION OF THE INVENTION

The present process is suitable for the partial dimerization of organic diisocyanates having aliphatically- and/or cycloaliphatically-bound isocyanate groups. Suitable starting diisocyanates for the present process are particularly aliphatic or cycloaliphatic diisocyanates having a molecular weight of more than 139, preferably from 140 to 250, such as tetramethylene diisocyanate, hexamethylene diisocyanate, dodecamethylene diisocyanate, cyclobutane-1,3-diisocyanate, cyclohexane-1,3- and -1,4-diisocyanate, 1-isocyanato-3,3,5-trimethyl-5-isocyanatomethyl-cyclohexane (IPDI), perhydro-2,4- and/or -2,6-diisocyanato-toluene or perhydro-2,4'- and/or -4,4'-diisocyanato-diphenyl methane or mixtures of these diisocyanates.

1,6-diisocyanato-hexane (hexamethylene diisocyanate) is most preferably used as starting diisocyanate.

The present process is preferably carried out in the absence of solvent at a temperature of about 0° to 80° C., particularly about 10° to 50° C.

The catalyst essential to the present invention, antimony(V)fluoride, is a known chemical and is described for example, in "Gmelins Handbuch der anorganischen Chemie", 8th Edition, System Number 18 (1949), page 401. The catalyst is used in a quantity of about 0.2 to 5%, by weight, preferably about 0.5 to 2%, by weight, based on starting diisocyanates.

The dimerization reaction is preferably carried out within the above temperature range until a degree of dimerization of about 5 to 35, preferably about 10 to 25, has been reached. The term "degree of dimerization" is to be understood in this context as designating the percentage of isocyanate groups in the starting diisocyanate which are converted into uretdione groups. The degree of dimerization may be monitored during the dimerization reaction by, for example, continuously determining the refractive index or the NCO content of the reaction mixture.

After the desired degree of dimerization has been reached, the dimerization reaction is preferably stopped by addition of a catalyst poison. The dimerization reaction may also be stopped by the removal of the dimerization catalyst by distillation, together with excess, unreacted starting diisocyanate, for example. The desired degree of dimerization within the above ranges is generally reached after a period of about 3 to 72 hours, depending on the quantity of catalyst and the reaction temperature.

Suitable catalyst poisons are compounds which, as given in the above literature, are chemically-reactive with antimony(V)fluoride or adsorptively bind antimony(V)fluoride on the surface thereof. Amounts of solids which may be produced at this point may be removed from the reaction mixture by filtration, for example. Suitable catalyst poisons include organic carboxylic acids (i.e. organic compounds which contain at least one free carboxyl group such as tartaric acid, phthalic acid, benzoic acid or the mono-potassium salt of tartaric acid), zinc powder or sulphur. The monopotassium salt of tartaric acid is most preferably used as catalyst poison. The quantity of catalyst poison is preferably calculated such that it suffices for the complete "neutralization" of the catalyst. This quantity may, for example, be determined by a preliminary test.

Following the dimerization reaction, the products may, if desired, be freed from unreacted starting diisocyanate by thin layer distillation to a residual content of less than about 1%, based on the total mixture. As explained above, this removal by distillation of unreacted starting diisocyanate may also be combined with the termination of the dimerization reaction by the removal of the catalyst by distillation. Stopping the dimerization reaction in this manner is, however, less preferred than by the addition of a catalyst poison.

The present products are also low viscous substances at room temperature, after removal of excess starting diisocyanate, which do not have isocyanurate groups according to IR spectroscopy. The NCO content is only slightly (up to at most 20%) below the theoretical value calculated from the formula:

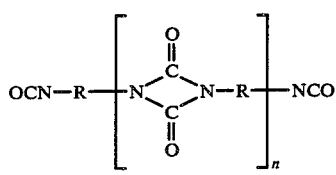

wherein n equals 1. In this formula, R represents the residue of the starting diisocyanate R(NCO)$_2$. This slight deviation from the theoretical value is based on the presence of oligomeric uretdione diisocyanates (n=an integer greater than 1, preferably from 2 to 5).

The present products may, of course, be blocked in known manner with suitable blocking agents for isocyanate groups such as phenol, ε-caprolactam, malonic acid diethyl ester or acetoacetic acid ethyl ester.

The present products or the derivatives thereof obtained by the above blocking reaction are valuable starting materials for the production of polyurethane plastics according to the isocyanate polyaddition process. They are particularly suitable as isocyanate components in two-component polyurethane lacquers. Owing to the presence of uretdione groups, which are considered as masked isocyanate groups, the present products are particularly suitable for the production of heat-cross-linkable coatings.

The following examples illustrate the present invention. All percentages relate to percentage, by weight, unless otherwise indicated. All "parts" relate to parts by weight.

EXAMPLES

EXAMPLE 1

100 parts of hexamethylene diisocyanate and 1 part of antimony(V)fluoride were stirred at room temperature for 40 hours after which the NCO content had dropped to 41.9%. The reaction was stopped by the addition of 5 parts of zinc powder. The mixture was then stirred for 2 hours and filtered. 31 parts of isocyanato-uretdione having the following characteristics were obtained after thin layer distillation:

NCO content 22.3%; free hexamethylene diisocyanate >0.6%: viscosity (23° C.): 70 mPas.

EXAMPLE 2

100 parts of hexamethylene diisocyanate and 0.5 parts of antimony(V)fluoride were stirred for 5 hours at 50° C. Thereafter, the refractive index had increased $n_D^{24°~C.}$ 1.4610 (starting value = $n_D^{21°~C.}$: 1.4530) and the NCO content had dropped to 43%. 22 parts of isocyanato-uretdione having the following characteristics were obtained after thin layer distillation:

NCO content 22.0%; free hexamethylene diisocyanate >1.0%; viscosity (23° C.) 60 mPas.

EXAMPLE 3

100 parts of hexamethylene diisocyanate and 0.8 parts of antimony(V)fluoride were maintained at 20° C. for 60 h. Thereafter, the refractive index $n_D^{23°~C.}$ 1.4650 had increased and the NCO content was 39.7%. The reaction was stopped by addition of 2 parts of tartaric acid-monopotassium salt. The mixture was then stirred for a further 2 h and filtered. 35 parts of isocyanato-uretdione having the following characteristics were obtained after thin layer distillation:

NCO content 22.5%: free hexamethylene diisocyanate >0.6%; viscosity 70 mPas.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of a uretdione group-containing polyisocyanate having aliphatically- and/or cycloaliphatically-bound isocyanate groups which comprises dimerizing a portion of the isocyanate groups of an organic diisocyanate having aliphatically- and/or cycloalphatically-bound isocyanate groups in the presence of antimony(V)fluoride and terminating the dimerization reaction when the desired degree of dimerization has been reached by the addition of a catalyst poison or by the removal of antimony(V)fluoride by distillation.

2. The process of claim 1 wherein said organic diisocyanate is 1,6-diisocyanato-hexane.

3. The process of claim 1 which comprises removing unreacted diisocyanate by thin layer distillation on completion of the dimerization reaction.

4. The process of claim 2 which comprises removing unreacted diisocyanate by thin layer distillation on completion of the dimerization reaction.

5. The process of claim 1 wherein said catalyst poison is an organic carboxylic acid, zinc powder or sulphur.

6. The process of claim 2 wherein said catalyst poison is an organic carboxylic acid, zinc powder or sulphur.

7. The process of claim 3 wherein said catalyst poison is an organic carboxylic acid, zinc powder or sulphur.

8. The process of claim 4 wherein said catalyst poison is an organic carboxylic acid, zinc powder or sulphur.

* * * * *